US005552462A

United States Patent [19]

Yeh

[11] Patent Number: 5,552,462
[45] Date of Patent: Sep. 3, 1996

[54] COMPOSITIONS INCLUDING CATIONIC POLYMERS AND ANIONIC XANTHAN GUM

[75] Inventor: Michael H. Yeh, Hamilton, N.J.

[73] Assignee: Rhone-Poulenc Inc., Monmouth Junction, N.J.

[21] Appl. No.: 156,189

[22] Filed: Nov. 22, 1993

[51] Int. Cl.$^6$ .............. C08L 5/00; C09D 4/00; C09J 4/00; C07H 11/04
[52] U.S. Cl. ............ 524/55; 524/56; 106/162.2; 106/205.1; 106/205.2; 252/315.01; 536/117; 536/118; 536/119; 536/123
[58] Field of Search ............ 524/55, 56; 106/208, 106/205; 252/315.01; 536/118, 123, 117, 119

[56] References Cited

U.S. PATENT DOCUMENTS

| | | | |
|---|---|---|---|
| 3,236,831 | 2/1966 | Schweiger | 260/209 |
| 3,467,647 | 9/1969 | Benninga et al. | 260/209 |
| 3,507,664 | 4/1970 | Schuppner, Jr. | 99/139 |
| 3,519,434 | 7/1970 | Schuppner, Jr. | 99/107 |
| 3,557,016 | 1/1971 | Schuppner, Jr. | 252/316 |
| 3,659,026 | 4/1972 | Schuppner, Jr. | 424/361 |
| 3,748,201 | 7/1973 | Jordan | 149/109 |
| 4,038,206 | 7/1977 | Karl | 252/316 |
| 4,162,925 | 7/1979 | Tiefenthaler et al. | 106/208 |
| 4,264,322 | 4/1981 | Lewis | 8/479 |
| 4,454,617 | 6/1984 | Moates | 8/151 |
| 4,487,866 | 12/1984 | Almond et al. | 524/42 |
| 5,104,487 | 4/1992 | Taggart et al. | 162/168.3 |
| 5,378,830 | 1/1995 | Yeh | 536/118 |

FOREIGN PATENT DOCUMENTS

| | | | |
|---|---|---|---|
| 2242401 | 3/1975 | France . | |
| 1518731 | 6/1969 | Germany . | |
| 281966A5 | 8/1990 | Germany | B01F 17/00 |
| 2064568 | 6/1981 | United Kingdom | C08B 37/00 |

*Primary Examiner*—Paul R. Michl
*Assistant Examiner*—LaVonda R. DeWitt
*Attorney, Agent, or Firm*—Andrew M. Solomon

[57] ABSTRACT

A novel blend composition comprising one or more cationic polygalactomannas and xanthan gum is provided. The blend is capable of producing enhanced viscosities when distributed in a solvent. The blend is suitable for use in foods, explosives, oil field chemicals, textile fibers, agricultural chemicals and cosmetics.

23 Claims, No Drawings

COMPOSITIONS INCLUDING CATIONIC POLYMERS AND ANIONIC XANTHAN GUM

BACKGROUND OF THE INVENTION

1. Field of the Invention

The present invention relates to a composition which includes both one or more cationic polymers and anionic xanthan gum. More specifically, the composition includes polygalactomannans which are cationically charged in combination with anionic substituted xanthan gum. The resulting compositions exhibit enhanced viscosities as compared to the viscosities obtained when using the polygalactomannans and xanthan gum separately or as compared to the viscosity of using polygalactomannans in combination with nonionic xanthan gum.

2. Technology Description

Natural and synthetic gums have been used as thickeners for foods, coatings, paints, explosive slurries, oil well fluids, cosmetics, and many other functional applications. One natural gum that has been widely used as a suspending and viscosity agent is xanthan gum. Aqueous sols of xanthan gum are plastic in nature and exhibit higher gel strengths than sols of most other gums. Blends of xanthan gum with other gums are known and each blend exhibits properties unique unto itself. One set of gums which has been suggested for blending with xanthan gum are the galactomannans.

For example, Schuppner et al in U.S. Pat. Nos. 3,507,664; 3,519,434; 3,557,016; and 3,659,026 discuss a number of uses for compositions which include both xanthan gum and locust bean gum. Amongst the uses mentioned are: milk gels (U.S. Pat. No. 3,507,664), meat gels (U.S. Pat. No. 3,519, 434), heat reversible gels in general (U.S. Pat. No. 3,557, 016) and agricultural uses (U.S. Pat. No. 3,659,026). A basic concept of each of these patents is that the combination of xanthan gum with locust bean gum for each of the functional applications yields a composition which, when displaced in a solvent, demonstrates excellent gelling attributes.

U.S. Pat. No. 4,038,206 suggests that higher viscosities can be obtained when the locust bean gum used in combination with xanthan gum is a hydroxyalkyl locust bean gum. The hydroxyalkyl locust bean gums include the water soluble hydroxypropyl ethers of locust bean gum, hydroxyethyl ethers of locust bean gum and hydroxybutyl ethers of locust bean gum. The hydroxyalkyl locust bean gum is prepared by reacting an alkylene oxide with locust bean gum to form one or more ether linkages. The suggested molar amount of alkylene oxide per mole of locust bean gum is 0.05 to 0.5.

U.S. Pat. No. 4,162,925 suggests that phosphated esters of locust bean gum having a degree of substitution ranging from about 0.03 to about 0.5 be used in combination with xanthan gum to form viscous liquids and/or firm gels. These materials are particularly suggested for use as suspending agents for oil well drilling and for use in precision planting procedures referred to as fluid drilling. The examples of the patent suggest that the phosphated esters utilized are anionic in nature.

The combination of xanthan gum with other galactomannans, such as guar gum and those derived from guar gum are also discussed in the literature. For example, U.S. Pat. No. 3,748,201 suggests thickening compositions containing xanthan gum and hydroxyalkyl ethers of guar gum. The hydroxyalkyl ether of guar gum is prepared by reacting guar gum with an alkylene oxide in the presence of an alkaline catalyst. The preferred degree of substitution of the guar gum resulting from the formation of ether linkages is preferably between about 0.2 to about 1.2. The compositions are suggested for use in dyeing yarns for carpeting and for explosives.

It is hypothesized that the interaction between xanthan gum and the above described polygalactomannans is of a molecular nature. Polygalactomannans with less galactose side-chains and/or less uniform distribution of galactose units will interact with xanthan gum more strongly than the polygalactomannans with higher galactose content and/or more uniform distribution of galactose over the mannan main chain.

U.S. Pat. No. 3,467,647 disclose polysaccharides containing both cationic and anionic substituents. Amongst the starting polysaccharides which are then modified according to this patent include starches, locust bean gum (carob gum) and guar gum. Cationic substituents include primary, secondary, or tertiary amino groups or quaternary ammonium, sulfonium or phosphinium groups. Suggested anionic substituents include carboxyl, sulfonate, sulfate or phosphate groups. Example 9 of this patent discloses guar gum as the polysaccharide, trimethylammoniumhydroxypropyl as the cationic groups, and phosphates as the anionic groups. The degree of substitution for each of these groups in this example is 0.05.

Chem. Abstracts CA115(16):16250p discusses the uses of certain polymer combinations which provide enhanced viscosities as compared to the viscosities of the individual polymers. Combinations mentioned include poly(styrene sulfonate) and either xanthan gum or hydroxyethyl cellulose, poly(vinyl sulfonate) and xanthan gum, a quaternary-ammonium-salt modified guar and either hydroxypropyl guar or hydroxyethyl cellulose, and a sulfonated guar and either hydroxyethyl cellulose or carboxymethylhydroxyethyl cellulose. These combinations are suggested for use in oil recovery.

Similarly, DD 281966 discloses a gel former which has both cationic and anionic polymers and provides a synergistic increase in viscosity as compared to solutions which contain separate amounts of the polymers. The anionic polymer is preferably a poly(dimethyl-diallylammonium chloride) containing pyrrolidinium units and the cationic polymer is preferably carboxymethylcellulose with a degree of substitution of 0.6–1.2.

U.S. Pat. Nos. 4,264,322; 4,403,360 and 4,454,617 disclose dye compositions for textile fibers. The compositions comprise an admixture of immiscible gel phases, wherein one gel phase is thickened with a cationic gelling agent and wherein a second gel phase, which is dispersed in the first gel phase, is thickened with an anionic gelling agent. Suggested cationic gelling agents for the first phase include cationic polygalactomannans containing quaternary ammonium ether substituents. Suggested anionic gelling agents for the second phase include hydrocolloids which have the same type of basic polymeric structure as the cationic gelling agents, except that in place of the cationic group there is substituted an anionic group such as a carboxylic acid, sulfonic acid, or sulfate.

DE 1,518,731 discloses that galactomannans or glucomannans may be etherified with β-halogen ethane sulfonic acid or halogen methane sulfonic acids in the presence of base to yield compositions which can function as textile finishes, sizes and print thickeners.

U.S. Pat. No. 3,912,713 and FR 2,242,401 disclose guar gum derivatives and processes for preparing the derivatives.

The derivatives are prepared by adding a substituent to guar gum splits in the presence of water, and typically, base. Amongst the substituents (derivatizing agents) suggested for use in these patents are haloalkylsulfonic acids, such as bromoethanesulfonic acid and chlorohydroxypropanesulfonic acid, epoxyalkyl sulfonic acids, such as epoxypropane sulfonic acid, and $\alpha$, $\beta$-alkylene sulfonic acids, such as ethylene sulfonic acid. These compounds are suggested for use as thickening agents, stressing, sizing and finishing agents, protective colloids and as agents for stabilizing dispersions and emulsions.

U.S. Pat. No. 4,031,305 discloses sulfohydroxypropyl ethers of polygalactomannans having a degree of substitution between about 0.01 and 3. The ethers are prepared by contacting solid guar gum or locust bean gum with a 3-halo-2-hydroxypropanesulfonic acid or acid salt in the presence of base. The galactomannan ethers are alleged to be anionic in nature and are proposed for use in petroleum, textile, printing, paper, food and pharmaceutical industries.

U.S. Pat. No. 4,057,509 discloses the formation of an acidic gel by contacting a polygalactomannan with an allyl halide, followed by exposing the formed polygalactomannan allyl ether material to a stream of sulfur dioxide. The gels are suggested for use in oil well drilling mud compositions and oil well fracturing compositions.

Despite the above, there still is a need for compositions which demonstrate enhanced viscosity behavior and which rely on forces in addition to molecular ones.

BRIEF SUMMARY OF THE INVENTION

In accordance with the present invention, a novel combination which demonstrates enhanced viscosity behavior than each of the starting polymers and which utilizes both ionic and molecular forces is provided. The novel combination comprises anionic substituted xanthan gum and one or more cationic polymers.

One embodiment of the present invention comprises a blend composition comprising about 1 to about 99 parts of one or more cationic polymers, preferably a polygalactomannan having a degree of substitution of about 0.01 to about 3.00 and about 1 to about 99 parts of anionic substituted xanthan gum.

In particularly preferred embodiments, the cationic polymer is a polygalactomannan having a degree of substitution between about 0.01 and about 1.00, and the anionic nature of the xanthan polymer is formed by substituting anionic sulfonate groups derived from ethylenically unsaturated polymers onto the xanthan backbone.

The blends are particularly effective as thickening agents. They may be used for a number of functional applications such as in foods, explosives, oil field chemicals, agricultural applications, cosmetics and the like.

Another embodiment of the present invention comprises a process for producing a viscous liquid or a gel. The process comprises the step of adding to a solvent, preferably water, 0.1 parts to about 2.0 parts per 100 parts viscous liquid or gel of a blend composition having a ratio of about 1 to about 99 parts of one or more cationic polymers and about 1 to about 99 parts of anionic substituted xanthan gum.

A third embodiment of the present invention comprises a food, explosive, oil field chemical, agricultural chemical, textile fiber or cosmetic including an amount of a blend composition having a ratio of about 1 to about 99 parts of one or more cationic polymers and about 1 to about 99 parts of anionic substituted xanthan gum.

Accordingly, it is an object of the present invention to provide a novel blend composition which comprises materials which, in combination, demonstrate a superior viscosity profile as compared to the materials individually or uncharged combined materials.

It is another object of the present invention to provide a process for producing a viscous liquid or gel using a novel blend composition.

A further object of the present invention to provide a food, explosive, oil field chemical, agricultural chemical, textile fiber or cosmetic which includes the novel blend composition.

These, and other objects, will readily be apparent to those skilled in the art as reference is made to the detailed description of the preferred embodiment.

DETAILED DESCRIPTION OF THE PREFERRED EMBODIMENT

In describing the preferred embodiment, certain terminology will be utilized for the sake of clarity. Such terminology is intended to encompass the recited embodiment, as well as all technical equivalents which operate in a similar manner for a similar purpose to achieve a similar result.

The present invention comprises an amphoteric polysaccharide blend composition comprising about 1 to about 99 parts of one or more cationic polymers, preferably polygalactomannans having a degree of substitution of about 0.01 to about 3.00 and about 99 to about 1 parts of anionic substituted xanthan gum. In practice the materials may be mixed together in a dry state or, more preferably, each distributed in a fluid, preferably water, and each fluid is then mixed together.

The first component of the blend comprises one or more cationic polymers, preferably polygalactomannans having a degree of substitution of between about 0.01 and about 3.0. Particularly preferred are cationic polygalactomannans having a degree of substitution of between about 0.05 and about 2.0, with a degree of substitution of between about 0.1 and about 1.0 being most preferred.

The polygalactomannans are polysaccharides composed principally of galactose and mannose units and are usually found in the endosperm of leguminous seeds, such as guar, locust bean, honey locust, flame tree, and the like. Guar flour, for example, is composed mostly of a galactomannan which is essentially a straight chain mannan with single membered galactose branches. The mannose units are linked in a 1-4-$\beta$-glycosidic linkage and the galactose branching takes place by means of a 1-6 linkage on alternate mannose units. The ratio of galactose to mannose in the guar polymer is, therefore, one to two. Guar gum has a molecular weight of about 1.5 million.

Locust bean gum is also a polygalactomannan gum of similar molecular structure in which the ratio of galactose to mannose is one to four. Guar and locust bean gum are the preferred sources of the polygalactomannans, principally because of the commercial availability thereof.

In use the polygalactomannan may be either in its natural state (i.e., pure guar gum or locust bean gum) or may be derivatized. Derivatized polygalactomannans include one or more non-ionic groups. Examples of such polygalactomannans include hydroxypropyl guar, hydroxyethyl guar, and the like. Such derivatized polygalactomannans are sold by Rhône-Poulenc Inc. under the trade names Jaguar 8012, Jaguar 8060, Jaguar 8000, Jaguar HP-20 and Jaguar HP-23.

By the term "degree of substitution" as employed herein is meant the average substitution of cationic or anionic groups per anhydro sugar unit in the polygalactomannan gums. In guar gum, the basic unit of the polymer consists of two mannose units with a glycosidic linkage and a galactose unit attached to a hydroxyl group of one of the mannose units. On the average, each of the anhydro sugar units contains three available hydroxyl sites. A degree of substitution of three would mean that all of the available hydroxyl sites have been esterified with formate ester groups.

Alternative materials which may be selected as the starting polymer material before substituted with one or more cationic groups include starches, celluloses and xanthan gum. Examples of starches include both natural and modified starches, such as dextrinated, hydrolyzed, oxidized, cross-linked, alkylated, hydroxyalkylated, acetylated, or fractionated (e.g., amylose and amylopectin). The starch may be of any origin, for example, corn starch, wheat starch, potato starch, tapioca starch, sago starch, rice starch, waxy corn starch or high-amylose corn starch.

Examples of celluloses include hydroxyethyl cellulose, hydroxypropyl cellulose, and alkyl celluloses.

Illustrative cationic groups suitable for the practice of the present invention include quaternary ammonium groups. Typical of quaternary ammonium groups are tetramethylammonium chloride and bromide, benzyltrimethylammonium chloride and bromide, tetraethylammonium chloride and bromide, tetrabutylammonium chloride and bromide, methylpyridinium chloride and bromide, benzylpyridinium chloride and bromide, trimethyl-p-chlorobenzylammonium chloride and bromide, and the like, wherein each of the said groups is derivatized in the form of a radical which is substituted in a hydrocolloid gelling agent by means of an alkylene or oxyalkylene linkage.

The polymeric structure of suitable polygalactomannans including cationic groups include vinyl polymers and copolymers, ion exchange resins, polysaccharides, and the like. Illustrative of this class of hydrocolloids are polygalactomannan gums containing quaternary ammonium ether substituents as described in U.S. Pat. No. 4,031,307:

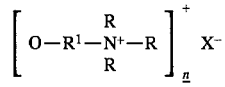

wherein R is an alkyl group containing between one and about six carbons atoms, $R^1$ is an alkylene group containing between one and about six carbon atoms, X is chlorine or bromine, and n is an integer which correlates with the degree of substitution of the quaternary ammonium ether substituents in a polygalactomannan gum cationic gelling agent. The said alkyl and alkylene group can contain other atoms such as oxygen, sulfur and halogen.

The cationic derivatives of guar gum or locust bean gum are prepared by contacting solid guar gum or locust bean gum with a haloalkyl-substituted quaternary ammonium compound and a stoichiometric excess of alkali metal hydroxide or ammonium hydroxide in a reaction medium comprising an aqueous solution of water-miscible solvent, at a temperature between about 10° C. and about 100° C. for a reaction period sufficient to achieve a degree of substitution by quaternary ammonium ether groups between about 0.01 and about 0.40.

The solid guar gum or other polygalactomannan which is etherified can be in the form of endosperm splits or in the form of finely divided powder which is derived from the endosperm splits. It is important that the polygalactomannan gum being etherified with quaternary ammonium groups remains as a solid phase in the reaction medium during the reaction period.

Further details on the synthesis of these polymers are provided in U.S. Pat. No. 4,031,307. To the extent necessary, this patent is incorporated by reference.

Examples of commercially available polygalactomannans having one or more substituted cationic quaternary ammonium groups include Jaguar C-13, Jaguar C-13S, Jaguar C-14, Jaguar C-17 and Jaguar C-14S, all sold by Rhône-Poulenc Inc.

Other cationic polymers include those which contain other cationic groups such as acid salts of primary, secondary, and tertiary amines, sulfonium groups or phosphonium groups.

The other component of the inventive blend composition comprises xanthan gum which contains anionic charges, preferably by the substitution of anionic groups onto the xanthan molecular backbone. Xanthan gum is typically obtained from the fermentation product produced by the action of the bacteria *Xanthomonas campestris* upon carbohydrates. Other species of Xanthomonas are considered to be within the scope of the present invention. A discussion on the production of xanthan gum from a fermentation broth is provided in U.S. Pat. Nos. 4,041,234 and 4,299,825. To the extent necessary, these references are hereby incorporated by reference. Once the xanthan gum has been produced from the fermentation broth, it is typically separated from the broth, washed and dried. The xanthan gum particles are typically anionic in nature. Non-limiting examples of suitable xanthan gum particles useful in the present invention are sold under the trade names Rhodigel, Rhodopol 23P and Rhodopol 23 by Rhône-Poulenc Inc.

The anionic nature of the xanthan polymer is preferably obtained by the substitution of one or more sulfonate groups onto the xanthan backbone. Particularly preferred as anionic substituents are those derived from ethlyenically unsaturated monomers containing one or more sulfonate groups. Examples of such monomers include the sodium salt of 2-acrylamido-2-methylpropane sulfonic acid and the sodium salt of 1-allyloxy-2-hydroxypropylsulfonic acid. The former monomer is derived from 2-acrylamido-2-methylpropane sulfonic acid, which is commercially available from Lubrizol and sold under the trade name LZ 2401 and the later monomer is commercially available from Rhône-Poulenc Inc. and sold under the trade name Sipomer Cops I.

Other anionic groups which may be substituted onto the xanthan backbone include sulfate, carboxyl or phosphate groups.

The formation of ether linkages between the sulfonated substituent and the xanthan polymer occurs by directly adding the substituent to the xanthan gum, preferably in the presence of a solvent such as toluene. The reaction temperature generally is between about 10° C. and about 100° C. Reactivity of the polymer with the substituent may be aided by utilizing a small amount of an initiator. Examples of suitable initiators include ammonium persulfate. Ph buffers, such as disodium phosphate, may also be optimally added.

When blended or otherwise mixed together, the ratio of cationic polymer to anionic xanthan gum in this invention can be varied over a wide range, for example between about 1 to about 99 weight percent of the cationic polymer to between about 99 to 1 weight percent anionic xanthan gum, the total being 100 parts by weight. The preferred range is about 5 to about 95 parts by weight of cationic polymer to about 95 to about 5 parts by weight of anionic polymer, the total being 100 parts by weight.

In use, the inventive compositions can effectively function as thickeners when added to a solvent, typically water. This typically comprises adding between about 0.1 and about 2.0 parts of the anionic xanthan polymer and the cationic polymer per 100 parts of viscous liquid or gel.

The amphoteric polysaccharide blend compositions are typically produced by combining solutions of both cationic and anionic polymers in respective amounts so that the positive and negative charges are equally balanced. The respective amounts of anionic and cationic solutions are added together based primarily upon the degree of substitution of each. For example, larger amounts of a low degree of substitution cationic polymer solution may be added to smaller amounts of a high degree of substitution anionic solution.

While in the preferred embodiment, the amounts of anionic and cationic solutions are added in relative amounts to produce a charge neutral solution, the amounts of each may be varied to yield solutions which have an overall positive or negative charge. Although not as enhanced as when producing a charge neutral solution, some synergistic viscosity increasing effect is achieved by unbalanced charged additions.

As an alternative to mixing separate aqueous solutions of the cationic and anionic polymers to obtain the inventive amphoteric blend, the cationic polymer and the anionic xanthan gum may be mixed together in a dry state in the desired ratio and then added to the water as stated above. For easy handling and ready dispersibility, the gums should have a particle size of less then about 100 mesh. Other components, e.g., fillers, wetting agents, dispersants, bactericides, fungicides and the like can be mixed with the powdered blends of the invention if so desired.

The fact that interaction between different polygalactomannans can provide enhanced viscosities is known. What is surprising about this invention is that by utilizing cationic polymers in combination with anionic xanthan gum a dual advantage is achieved. The first advantage is the enhanced viscosity brought about by the molecular interaction of the cationic polymer with the anionic xanthan. The second advantage is the ionic interaction involved by using a cationic-polymer with the anionic xanthan gum. By utilizing both the molecular and ionic forces, truly improved results are obtained as compared to blends which utilize nonionic polysaccharides.

The novel compositions, due to their thickening properties, have a wide number of possible uses. Amongst them are as suspending agents for various solids, such as in oil field chemicals, for use in dyeing textile fibers, for use in foods, for use in cosmetics and personal care products, for use with agricultural products, for use is explosives, for use in paper production and the like. Other uses will readily be appreciated by those skilled in the art.

The invention is described in greater detail by the following non-limiting examples.

EXAMPLE 1

A solution of 2.4 parts ammonium persulfate and 3 parts disodium phosphate in 50 parts water is added to 322 parts of Rhodigel, xanthan gum manufactured by Rhône-Poulenc Inc. in 1300 parts toluene and the solution is heated to 70° C. 50 parts of a sodium 2-acrylamido-2-methylpropane sulfonate monomer solution are added and the reaction temperature is maintained at 65°–70° C. for two hours. The mixture is cooled, filtered and dehydrated with methanol. The yield is 370.8 parts, with a moisture content of 12%.

EXPERIMENTAL TEST DATA

The following samples are used to compare the viscosities of 1% aqueous solutions at 25° C. two hours after hydration under different shear conditions:

Sample A - Rhodigel (100%) (xanthan gum)

Sample B - Example 1 Composition (100%)

Sample C - Jaguar C-14 (100 %) (cationic guar)

Sample D - Jaguar C-17 (100%) (cationic guar)

Sample E - 50:50 weight mixture of Sample A and Sample C

Sample F - 50:50 weight mixture of Sample B and Sample C

Sample G - 50:50 weight mixture of Sample A and Sample D

Sample H - 50:50 weight mixture of Sample B and Sample D

The shear rates, in rpms, and the viscosities, in centipoises, are shown in Table 1.

TABLE 1

| RPM | 0.5 | 1 | 2.5 | 5 | 10 | 20 | 50 |
| --- | --- | --- | --- | --- | --- | --- | --- |
| Sample A | 50000 | 28500 | 13200 | 7600 | 4200 | 2400 | 1100 |
| Sample B | 68000 | 34000 | 17200 | 9200 | 5100 | 2800 | 1280 |
| Sample C | 32000 | 26000 | 18400 | 12800 | 8600 | 5500 | 2820 |
| Sample D | 10000 | 9000 | 6800 | 5200 | 3800 | 2650 | 1500 |
| Sample E | 57000 | 31500 | 14000 | 7800 | 4400 | 2500 | 1400 |
| Sample F | 68000 | 36000 | 16000 | 9200 | 5000 | 3300 | 2000 |
| Sample G | 148000 | 84000 | 36800 | 20000 | 10800 | 6200 | 2600 |
| Sample H | 152000 | 80000 | 39600 | 20800 | 12000 | 8000 | 3950 |

A review of the data in Table 1 demonstrates that Sample F, which is a mixture of cationic guar with anionic xanthan gum yields a higher viscosity at all shear rates as compared to Sample E, which is a mixture of cationic guar with unsubstituted xanthan gum. Although not as pronounced, Sample H, which is a mixture of a different cationic guar with anionic xanthan gum yields a higher viscosity, particularly at higher shear rates as compared to Sample G, which is a mixture of cationic guar with unsubstituted xanthan gum. Further, Sample B, which comprises anionic substituted xanthan gum, demonstrates higher viscosities than Sample A, which contains no such anionic substitution.

Having described the invention in detail and by reference to the preferred embodiments thereof, it will be apparent that modifications and variations are possible without departing from the scope of the appended claims.

What is claimed is:

1. A blend composition comprising about 1 to about 99 parts of one or more cationic polysaccharides and about 99 to about 1 parts of anionic substituted xanthan gum.

2. The composition according to claim 1 wherein each of said one or more cationic polysaccharides comprises a polygalactomannan having a degree of substitution of between about 0.01 and about 3.00.

3. The composition according to claim 2 wherein each of said one or more cationic polygalactomannans is derived from guar gum or locust bean gum.

4. The composition according to claim 3 wherein each of said one or more cationic polygalactomannans is derived from guar gum.

5. The composition according to claim 1 wherein the said one or more cationic polysaccharides and said anionic substituted xanthan gum are each separately added to a solvent to form solutions which are then mixed together.

6. The composition according to claim 1 wherein the cationic groups of said cationic polysaccharide are selected from the group consisting of quaternary ammonium groups, acid salts of primary, secondary, and tertiary amines, sulfonium groups and phosphonium groups and mixtures thereof.

7. The composition according to claim 6 wherein said anionic substituted group of said anionic substituted xanthan gum is selected from the group consisting of sulfonate groups, sulfate groups, carboxyl groups and phosphate groups.

8. The composition according to claim 7 wherein said anionic substituted group of said anionic substituted xanthan gum is derived from ethylenically unsaturated monomers including one or more sulfonate groups.

9. The composition according to claim 8 wherein said ethylenically unsaturated monomers are selected from the group consisting of 2-acrylamide-2-methylpropane sulfonic acid and 1-allyloxy-2hydroxypropyl sulfonic acid and salts thereof.

10. The composition according to claim 1 wherein the charges of said cationic polysaccharide and the charges of said anionic substituted xanthan gum are balanced to yield a charge neutral composition.

11. The composition according to claim 1 used in foods, explosives, oil field chemicals, personal care products, paper production, textile fibers and agricultural applications.

12. A process for producing a viscous liquid or gel comprising the step of adding to a solvent about 0.1 parts to about 2.0 parts per 100 parts viscous liquid or gel of a blend composition having a ratio of about 1 to about 99 parts of one or more cationic polysaccharides and about 1 to about 99 parts of an anionic substituted xanthan gum.

13. The process according to claim 12 wherein said solvent is water.

14. The process according to claim 13 wherein said one or more cationic polysaccharides is a polygalactomannan having a degree of substitution of between about 0.01 and about 3.00.

15. The process according to claim 14 wherein said cationic polygalactomannan is derived from guar gum or locust bean gum.

16. The process according to claim 15 wherein said cationic polygalactomannan is derived from guar gum.

17. The process according to claim 13 wherein the said one or more cationic polysaccharides and said anionic substituted xanthan gum are each separately added to a solvent to form solutions which are then mixed together.

18. The process according to claim 14 wherein the cationic groups of said cationic polygalactomannan are selected from the group consisting of quaternary ammonium groups, acid salts of primary, secondary, and tertiary amines, sulfonium groups and phosphonium groups and mixtures thereof.

19. The process according to claim 13 wherein said anionic substituted group of said anionic substituted xanthan gum is selected from the group consisting of sulfonate groups, sulfate groups, carboxyl groups and phosphate groups.

20. The process according to claim 19 wherein said anionic substituted group of said anionic substituted xanthan gum is derived from ethylenically unsaturated monomers including one or more sulfonate groups.

21. The process according to claim 20 wherein said ethylenically unsaturated monomers are selected from the group consisting of 2-acrylamido-2-methylpropane sulfonic acid and 1-allyloxy-2hydroxypropyl sulfonic acid and salts thereof.

22. The process according to claim 13 wherein the charges of said cationic polysaccharide and the charges of said anionic substituted xanthan gum are balanced to yield a charge neutral composition.

23. A food, explosive, personal care product, paper production chemical, oil field chemical, textile fiber or agricultural chemical including an amount of a blend composition having a ratio of about 1 to about 99 parts of one or more cationic polysaccharides and about 99 to about 1 parts of anionic substituted xanthan gum.

* * * * *